United States Patent [19]

Illy

[11] Patent Number: 5,350,123
[45] Date of Patent: Sep. 27, 1994

[54] SYSTEM FOR CONTROLLING THE GRINDING OF ROAST COFFEE

[75] Inventor: Ernesto Illy, Trieste, Italy

[73] Assignee: Illycaffe' S.p.A., Trieste, Italy

[21] Appl. No.: 681,257

[22] Filed: Apr. 8, 1991

[30] Foreign Application Priority Data

Apr. 24, 1990 [IT] Italy ................................ 20122 A/90

[51] Int. Cl.$^5$ ............................................. B02C 23/00
[52] U.S. Cl. ........................................ 241/37; 241/100
[58] Field of Search ............................ 241/37, 100, 60

[56] References Cited

U.S. PATENT DOCUMENTS

| | | | |
|---|---|---|---|
| 1,220,147 | 3/1917 | Wear et al. | 241/100 X |
| 2,699,899 | 1/1955 | Dale | 241/100 |
| 4,110,485 | 8/1978 | Grubbs et al. | |
| 4,659,023 | 4/1987 | Frei et al. | 241/100 X |
| 4,789,106 | 12/1988 | Weber | 241/100 X |

*Primary Examiner*—Mark Rosenbaum
*Assistant Examiner*—Frances Chin
*Attorney, Agent, or Firm*—Keil & Weinkauf

[57] ABSTRACT

A conveyor system for a coffee grinder for taking ground coffee from the grinder to the packing machinery, and a laser test-meter used to analyze the granulometry of ground coffee test samples and compare them with a granulometric reference sample that are known. The system of the invention includes improvements which include a first device which continually receives undisturbed ground coffee samples and delivers these samples to a second device in which a gas stream blows a stream of coffee grains down a tube to the test-meter and a second stream of gas flowing at right-angles to the tube disperses any partially aggregated particles before they reach the test-meter. A third device creates a pressurized safety area around each lens of the laser test-meter. The area is partly closed so that laser beams can freely pass, and gas under pressure enters the area preventing coffee grains from entering the area and disturbing the lens. A fourth device sucks the grains from the test area and delivers them into an eddy-chamber from which they are periodically transferred to the system for conveying ground coffee to the packing machinery.

5 Claims, 3 Drawing Sheets

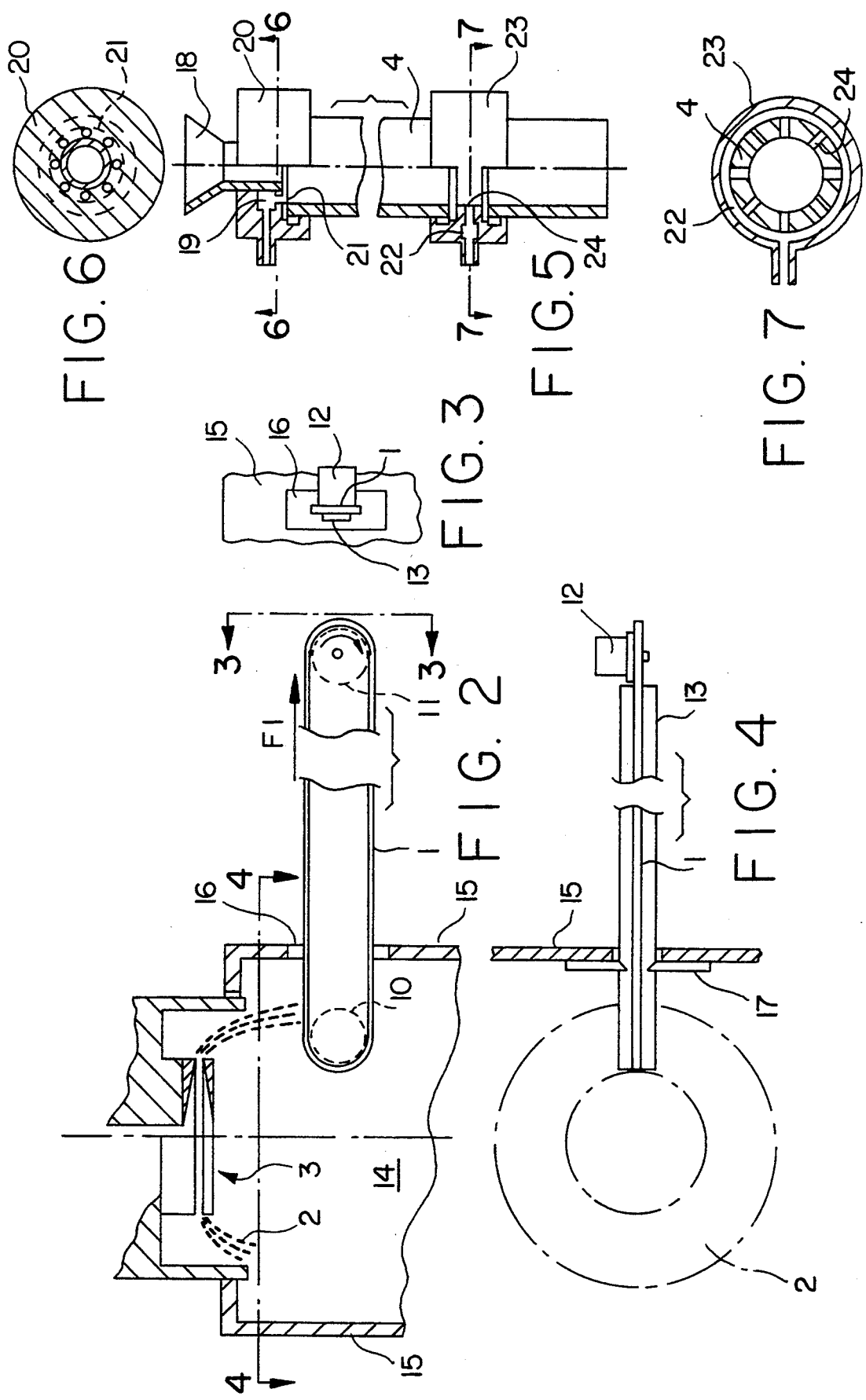

SYSTEM FOR CONTROLLING THE GRINDING OF ROAST COFFEE

This invention relates to a system for controlling the grinding of roast coffee.

'Espresso' coffee is made by rapidly extracting the substances contained in a compressed plug of ground roast coffee held in a filter using hot water at a considerable pressure. A number of different phenomena occur during extraction, the most important of which are: the dissolving of hydrosoluble substances in hot water, the emulsion of liposoluble substances in water with the help of surface-active substances which are naturally found in coffee, capilliary absorbtion of hot water by the coffee plug and a consequent increase in the volume of the plug, and the transport of microscopic coffee particles towards the base of the plug during the passage of the water and a consequent increase in resistance to the passage of water.

The above phenomena are influenced by the granulometry of the ground coffee, the specific surfaces of the granules, and by the degree of compaction of the plug.

It is therefore understood that the taste of an 'espresso' coffee depends on all the above factors, but from the point of view of the industrial production of ground roast coffee, keeping granulometry constant to an optimum granulometry model is of primary importance.

Generally speaking, to the best of the inventor's knowledge, the granulometry of ground coffee is checked, off the production line, by laser test-meters which check ground coffee samples and compare them with a granulometric reference sample. These test-meters have the defect of not providing complete and accurate information about granulometry during industrial production, as they operate on disturbed ground coffee samples.

The system that is the subject of the invention described here avoids the above disadvantage, and its advantages are set out in the description which follows.

This system for controlling the grinding of roast coffee includes a set of parts which are inserted into a coffee roasting, grinding, and packing system. There is, therefore, a coffee grinder and a conveyor system for taking ground coffee to the packing machinery. A laser test-meter is used to analyze the granulometry of ground coffee test samples and compare them with a granulometric reference sample. The system also includes a first device designed to continually receive undisturbed ground coffee samples and deliver these samples to a second device in which a gas stream blows a stream of coffee grains down a tube to the test-meter and a second stream of gas flowing at right-angles to the tube disperses any partially aggregated particles before they reach the test-meter. A third device creates a pressurized safety area around each lens of the laser test-meter. The area is partly closed so that laser beams can freely pass, and gas under pressure enters the area preventing coffee grains from entering the area and disturbing the lens. A fourth device sucks the grains from the test area and delivers them into an eddy-chamber from which they are periodically transferred to the system for conveying ground coffee to the packing machinery.

The main advantages of the invented system are; that the coffee samples delivered to the test-meter are as similar as is possible to the grains coming from the grinder, that as the laser test-meter is protected from all forms of dust and operates on de-aggregated coffee grains it provides an accurate reading, and lastly, that the coffee used by the test-meter is not lost.

One possible way that the invention can be constructed is described in detail in the part that follows, with reference to the drawings which show a specific way that the invention can be realized, and in which:

FIG. 2 is a schematic view of part of the first device;

FIG. 3 is a schematic part view from 3 to 3 in FIG. 2;

FIG. 4 is a schematic part plan view from 4 to 4 in FIG. 2;

FIG. 5 is a schematic elevation, partly sectional, of the second device;

FIG. 6 is a section from 6 to 6 in FIG. 5;

FIG. 7 is a section from 7 to 7 in FIG. 5;

Figure 1:
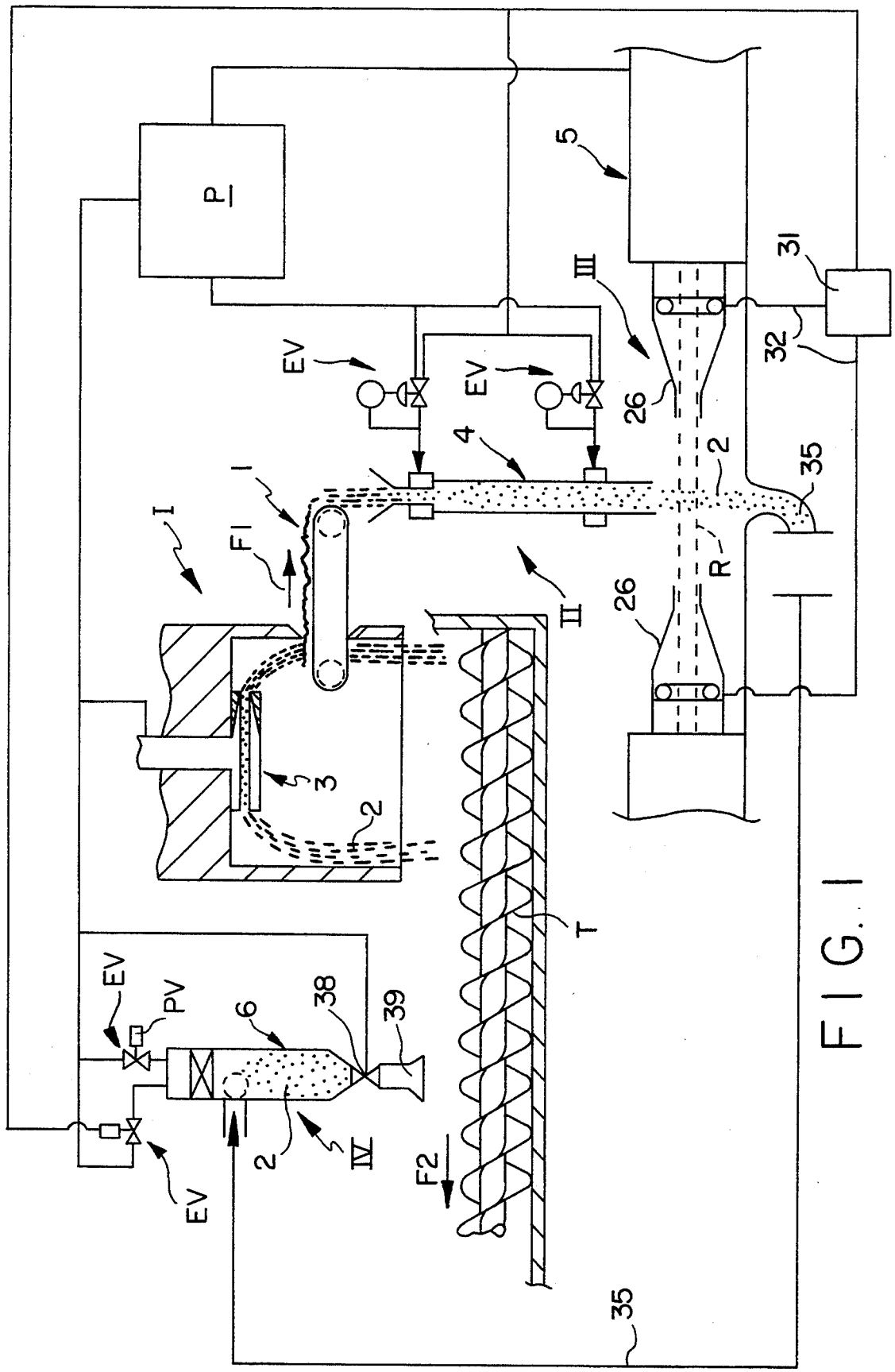
FIG. 1 is a schematic view of the entire system.

FIG. 1 shows the four devices (I, II, III, and IV) that make up the system, and the T-screw feeder used to transport ground coffee in the direction indicated by an arrow (F2) to a packing machine which is not shown. The first device (I) includes a conveyor belt (1) which receives samples of coffee (2) from a grinder (3) which is controlled by a programmer (P) connected to a test-meter (5) which emits laser beams (R). The first device drops the samples into the second device (II) includes a vertical tube (4) which receives compressed-air at its upper end from a supply source (31). The stream of air guides the coffee grains down the tube, and a second stream of compressed-air enters the tube at right-angles to the tube at a certain point along its length, and breaks up any aggregates. The third device (III) includes a test-meter (5) which uses laser beams (R). Each lens in the meter is protected from coffee grains (2) by a protection chamber (26), in which jets of air are directed at the outlet of the chamber thus preventing grains from entering. The fourth device (IV) includes an eddy-chamber (6) which receives the coffee grains (2) from the test-meter (5) and delivers them to the conveyor (T) (FIG. 1 also shows parts which are described in detail in the Figures that follow).

FIGS. 2, 3, and 4 show the first device in greater detail. It includes a conveyor belt (1) looped around a free running roller (10) and a drive roller (11) which is driven by an electric motor (12) in the direction shown by the arrow (F1). A bar structure (13), which is only shown in FIGS. 3 and 4, supports the two rollers (10 and 11) at its ends and the motor (12). One end of the conveyor belt (1) extends into the chamber (14) beneath the grinder (3) in order to receive ground coffee samples (2) which stream down, and its other end extends beyond the chamber (14) and deposits samples into the second device. There is an opening (16) in the side walls (15) of the chamber (14) through which the conveyor belt (1) and its support bar (13) pass.

It can be seen that as an alternative, the conveyor could be a scoop type conveyor into which ground coffee samples (2) are dropped and are then transported to and unloaded into the second device.

FIGS. 5, 6, and 7 show the second device (II) in greater detail. It includes a straight vertical tube with smooth internal walls (4) and the following parts:

a) There is a hopper (18) at its upper end which receives ground coffee samples dropped by the first device and drops them into the tube. The external diameter of the lower part of the hopper (18) is smaller than the internal diameter of the upper part of the tube (4), and forms the lower ring-shaped wall of a chamber (19) within a ring-shaped body (20) into which compressed-air from a supply source (31) flows. There are a number of holes (21) in the ring-shaped wall through which the compressed-air passes and then guides the still partly aggregated coffee grains down the tube.

b) There is a second pressurized air chamber (22) in an intermediate position along the tube, which has a ring-shaped body (23) around the tube and a number of radial holes (24) which connect it to the interior of the tube (4). A current of air passes from the chamber to the tube at right-angles to the tube, and creates sufficient turbulence to completely break down any aggregates of ground coffee, so that no aggregated ground coffee reaches the laser beam (R) and compromises the accuracy of its reading.

Figure 8:
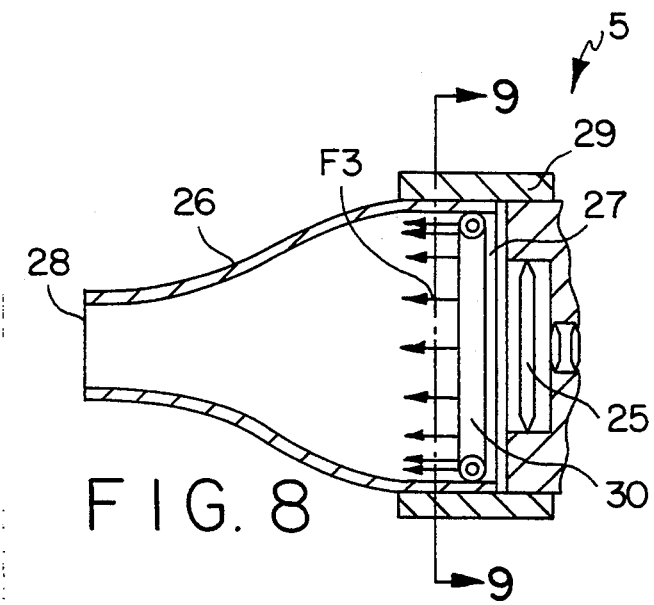
FIG. 8 is a part lengthwise section of the third device.
Figure 9:
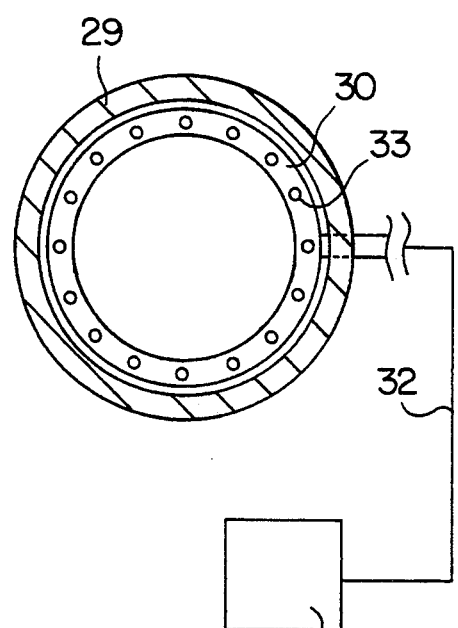
FIG. 9 is a part section from 9 to 9 in FIG. 8.

FIGS. 8 and 9 show the third device (III) in greater detail. It is designed to protect the lenses (25) of the laser beam test-meter (5), and creates a partly closed space around each lens formed by a casing (26) with two apertures (27 and 28). One aperture (27) is closed around the perimeter of the lens (25), and the other is open in front of the lens. A toriod-shaped duct (30) is positioned around the perimeter in front of the lens, and is connected to the compressed-air source (31) via a conduit (32). There are a number of holes (33) in the duct facing toward the second aperture (28), so that a current of air (shown by the arrows marked F3) is created which travels along the internal wall of the casing (26) from the lens to the open aperture (28) preventing any coffee grains from entering the casing (26).

Figure 11:
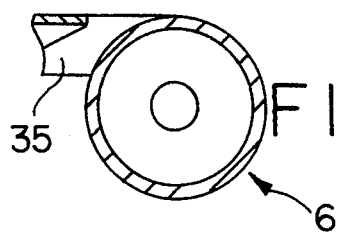
FIG. 11 is a schematic section from 11 to 11 in FIG. 10.
Figure 10:
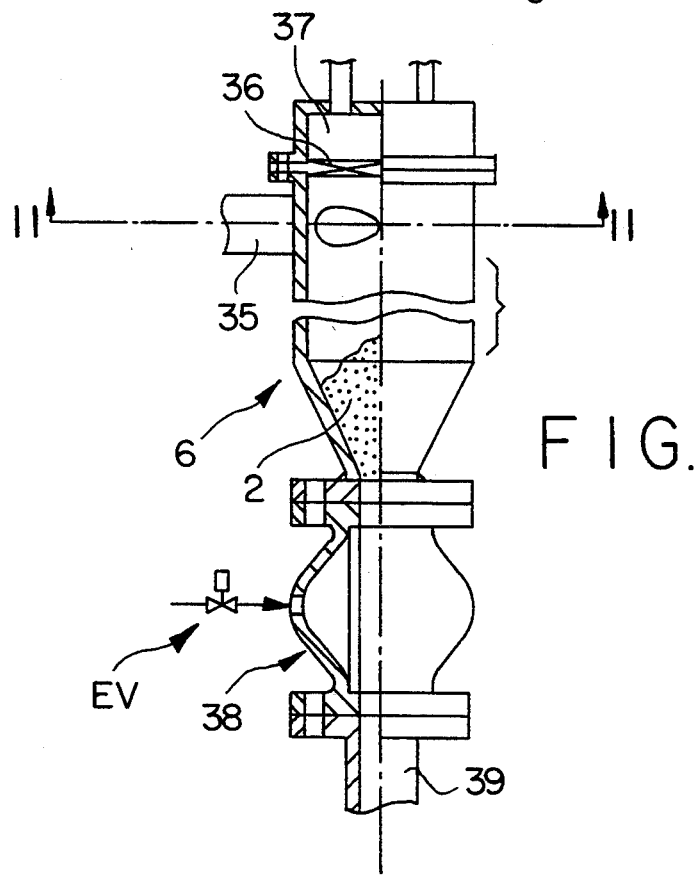
FIG. 10 is a partly sectional schematic elevation of the fourth device.

FIGS. 10 and 11 show the fourth device (IV) in greater detail. It includes an eddy-chamber (6) with a conduit (35) which arrives at an angle to its upper part through which coffee grains (2) falling from the third device (III) are delivered to the eddy-chamber. The upper part of the chamber (6) is closed off by a filter-baffle (36) creating an upper ground coffee-proof chamber (37) in which a compressed-air system controlled by solenoid-valves (schematically shown in FIG. 1 by the letters EV) and a programmer (P) can create a vacuum or pressurize the chamber. There is a compressed-air coupling valve (38) at the lower end of the eddy-chamber in which a vacuum or pressure is alternately created using a solenoid-valve (schematically shown by the letters EV) controlled by the programmer (P), and connected to a compressed-air system, such as the compressed-air supply (31). Thus, the fourth device collects the coffee grains that have been analysed by the test-meter by suction caused by the vacuum that has been created in the ground coffee-proof chamber (37) by a vacuum pump (PV) that is controlled by the solenoid-valves, and transfers it to the eddy-chamber (6) via the filter-baffle (36). The coffee grains sucked into the the eddy-chamber loose their kinetic energy and the eddy effect causes them to fall to the bottom of the chamber which is closed off by the coupling valve (38). They accumulate for a set time after which the vacuum is relieved, compressed-air is let in and the coupling valve (38) simultaneously opens allowing the ground coffee to fall through the lower outlet (39) of the eddy-chamber (6) into the device (T) used to convey ground coffee to the packing machinery.

I claim:

1. In a system for grinding roast coffee, testing the granulometry of the ground coffee, and conveying the ground coffee to a packaging machine, which system includes (1) a coffee grinding means wherein the granulometry is controlled by a programmer, (2) a testing means which uses laser beams to analyze the granulometry of the ground coffee and to compare the granulometry of the ground roast coffee with the granulometry of a reference sample of ground roast coffee, and (3) a conveyor means for transporting the ground roast coffee from the grinding means to a packaging means, the improvements comprising: a) a transporting means which transports samples of roast ground coffee from the stream of ground roast coffee coming from the grinding means to a vertical tube, which vertical tube leads to a test area of a test meter; b) the vertical tube is adapted by means of apertures in the perimeter of the tube to receive a downward flow of pressurized gas, which pressurized gas transports the ground coffee along the tube to the test area of the test meter, the vertical tube is further adapted by means of radial apertures to receive a second pressurized gas which flows at right angles to the tube, which gas breaks down any aggregates of ground coffee before the ground coffee falls into the test area of the test meter; c) the test meter containing a plurality of lenses through which laser beams pass; d) a compressed air source which is arranged to create a pressurized gas volume in the area around each lens of the test meter so that the ground coffee is prevented from entering the area around each lens; e) a suction means which is arranged to recover the ground coffee from the test area of the test meter and to deposit the recovered ground coffee in a container; and f) the container being positioned to hold the received ground coffee and to periodically release the held ground coffee and to return the ground coffee to the transporting means which conveys the coffee to the packaging machine.

2. A system as set forth in claims 1 wherein, the transporting means is a closed loop conveyor belt, one portion of which is so positioned under the grinding means to receive ground coffee samples exiting from the grinding means, and another portion of which is positioned above the vertical tube so as to deposit the received ground coffee samples into the vertical tube.

3. A system as set forth in claim 1 wherein, the vertical tube comprises a hopper at its upper end for receiving samples of ground coffee, the lower external diameter of the hopper being less than the upper internal diameter of the tube, and a chamber around an intermediate portion of the vertical tube, said chamber receives the second pressurized gas and transmits the second pressurized gas into the vertical tube through apertures which are at right angles to the axis of the tube.

4. A system as set forth in claim 1 wherein, the test area of the test meter is within a casing, which casing has two apertures.

5. A system as set forth in claim 1 wherein, the container is an eddy-chamber containing a) a conduit through which ground coffee from the test area of the test meter arrives, b) a filter in the upper part of the container which allows the passage of air but which does not allow the passage of ground coffee, which filter forms an upper chamber in the container into which ground coffee cannot enter; c) solenoid valves controlled by a programmer; d) air systems connected to the upper chamber which systems alternately (1) create a vacuum to suck ground coffee into the container and (2) pressurize the container, thus stopping the flow of the ground coffee; and e) a compressed air valve which is controlled by the programmer, which valve is at the lower extremity of the container, and which valve periodically opens to release ground coffee onto the conveyor means to be transported to the packaging machine.

* * * * *